Figure 1:
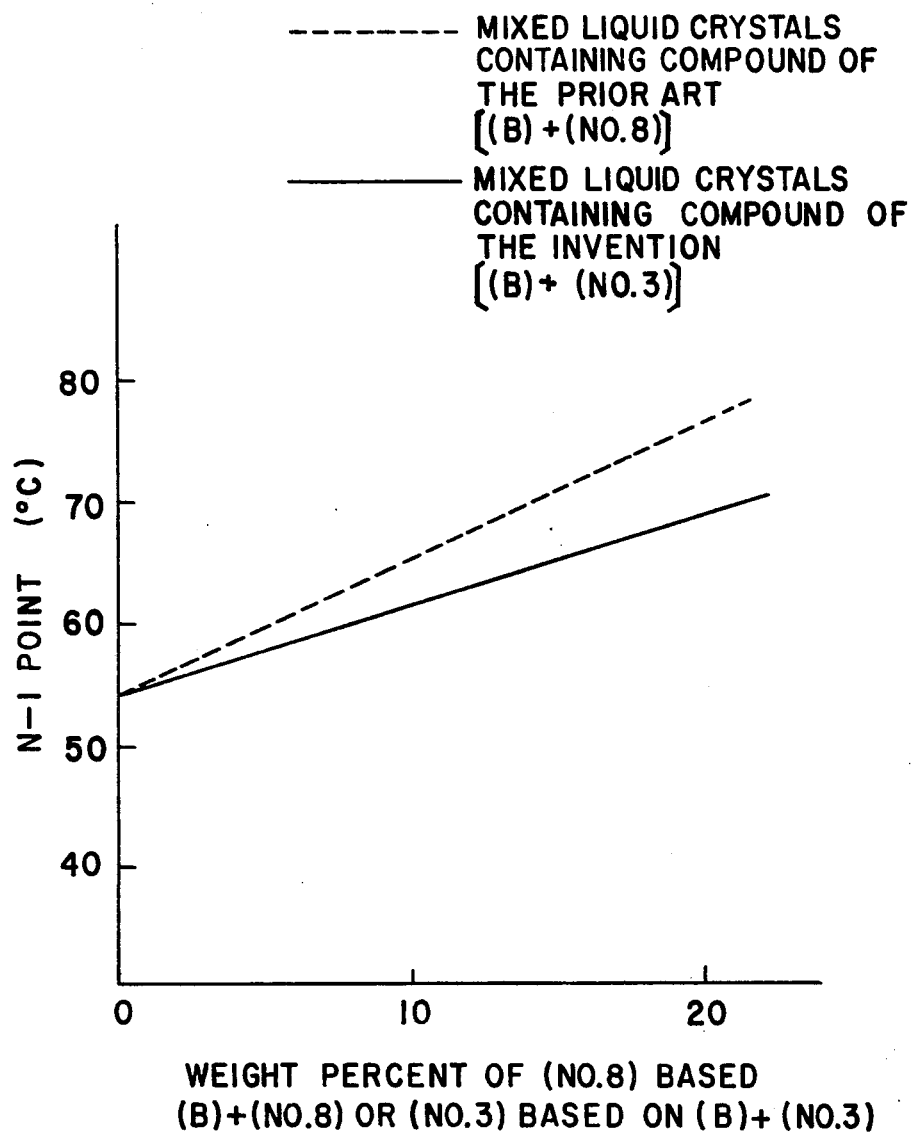

United States Patent [19]

Sato et al.

[11] 4,393,258
[45] Jul. 12, 1983

[54] 1-CYCLOHEXYL-2-CYCLOHEXYLPHEN-YLETHANE DERIVATIVES

[75] Inventors: Hisato Sato, Tokyo; Haruyoshi Takatsu, Kodaira; Yutaka Fujita, Yokohama; Masayuki Tazume; Kiyohumi Takeuchi, both of Urawa; Hiroyuki Ohnishi, Kawagoe, all of Japan

[73] Assignee: Dainippon Mk & Chemicals Inc., Tokyo, Japan

[21] Appl. No.: 386,994

[22] Filed: Jun. 10, 1982

[51] Int. Cl.³ .................. C07C 13/18; C07C 13/28
[52] U.S. Cl. .............................. 585/25; 585/26; 585/318; 585/320; 585/360; 585/456; 585/459; 252/299.01; 252/299.63
[58] Field of Search ............ 585/20, 23, 24, 25, 585/320, 317, 360, 361, 455, 456, 459; 252/299.01, 299.63

[56] References Cited

U.S. PATENT DOCUMENTS

| | | | |
|---|---|---|---|
| 4,029,595 | 6/1977 | Ross et al. | 252/299.63 |
| 4,195,916 | 4/1980 | Coates et al. | 252/299.01 |
| 4,229,315 | 10/1980 | Krause et al. | 252/299.63 |
| 4,237,026 | 12/1980 | Eidenschink et al. | 252/299.63 |
| 4,290,905 | 9/1981 | Kanbe | 252/299.63 |

Primary Examiner—Delbert E. Gantz
Assistant Examiner—A. Pal
Attorney, Agent, or Firm—Sherman & Shalloway

[57] ABSTRACT

A 1-cyclohexyl-2-cyclohexylphenylethane derivative of the following general formula

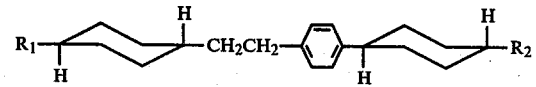

wherein $R_1$ and $R_2$, independently from each other, represent a linear alkyl group having 1 to 7 carbon atoms.

8 Claims, 3 Drawing Figures

1-CYCLOHEXYL-2-CYCLOHEXYLPHENYLE-THANE DERIVATIVES

This invention relates to novel nematic liquid crystalline compounds useful as electro-optical display materials.

The novel nematic liquid crystalline compounds provided by the present invention are 1-[trans(equatorial-equatorial)-4-n-alkylcyclohexyl]-2-[4-trans(equatorial-equatorial)-4'-n-alkylcyclohexylphenyl]ethanes of the following general formula

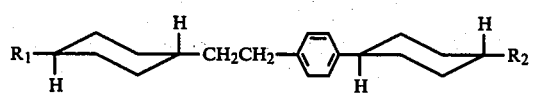

wherein $R_1$ and $R_2$, independently from each other, represent a linear alkyl group having 1 to 7 carbon atoms.

Typical liquid crystal display cells include field effect mode cells proposed by M. Shadt et al. [Applied Physics Letters, 18, 127–128 (1971)], dynamic scattering mode cells proposed by G. H. Heilmeier et al. [Proceedings of the I. E. E. E., 56, 1162–1171 (1968)] and guest-host mode cells proposed by G. H. Heilmeier et al. [Applied Physics Letters, 13, 91 (1968)] or D. L. White et al. [Journal of Applied Physics, 45, 4718 (1974)].

Liquid crystalline materials used in these liquid crystalline display cells are required to have various properties. One important property required commonly of all display cells is that such liquid crystalline materials have a nematic phase over a wide temperature range including room temperature. Many of practical materials having such a property are usually prepared by mixing several or more components consisting of compounds having a nematic phase at room temperature and compounds having a nematic phase at temperatures higher than room temperature. Many of mixed liquid crystals now in commercial use are required to have a nematic phase at least over a temperature range of from $-30°$ C. to $+65°$ C. In order to meet this requirement, there are frequently used compounds having a crystal-nematic phase transition temperature (C-N point) of about 100° C. and a nematic-isotropic liquid phase transition temperature (N-I point) of about 200° C., for example 4,4'-substituted terphenyls, 4,4'-substituted biphenylcyclohexanes and 4,4'-substituted benzoyloxybenzoic acid phenyl esters, as the compounds having a nematic phase at temperatures higher than room temperatures. These compounds, however, have the disadvantage of increasing the viscosities of the resultant mixed liquid crystals and thereby decreasing response speeds.

The compounds of formula (I) in accordance with this invention are novel compounds having improvements achieved in these properties. In preparing practical mixed crystals having an N-I point of at least 65° C. by mixing with at least one other nematic liquid crystalline compound, the aforesaid known liquid crystalline compounds, in many cases, greatly increase the viscosities of the resultant mixed crystals, whereas the compounds of formula (I) can favorably decrease them.

The compounds (I) of this invention can be produced, for example, by a two-step processs schematically shown below.

(II)

(III)

(IV)

(I)

In the first step, the compound of formula (II) is reacted with the compound of formula (III) and anhydrous aluminum chloride in carbon disulfide or nitrobenzene to form the compound of the formula (IV). In the second step, the compound (IV) is reacted with hydrazine and potassium hyroxide in diethylene glycol or triethylene glycol.

Typical examples of the compounds of formula (I) produced in this manner are given in Table 1 with their transition temperatures.

TABLE 1

| No. | $R_1$ | $R_2$ | Transition temperature (°C.) |
|---|---|---|---|
| 1 | $C_2H_5-$ | $n-C_3H_7-$ | 71(C→S)  81(S⇌N) 103(N⇌I) |
| 2 | $n-C_3H_7-$ | $C_2H_5-$ | 58(C→S)  78(S⇌N) 105(N⇌I) |
| 3 | $n-C_3H_7-$ | $n-C_3H_7-$ | 46(C→S) 106(S⇌N) 131(N⇌I) |
| 4 | $n-C_3H_7-$ | $n-C_4H_9-$ | 35(C→S) 117(S⇌N) 126(N⇌I) |
| 5 | $n-C_3H_7-$ | $n-C_5H_{11}-$ | 26(C→S) 131(S⇌N) 134(N⇌I) |
| 6 | $n-C_4H_9-$ | $n-C_3H_7-$ | 24(C→S) 114(S⇌N) 128(N⇌I) |
| 7 | $n-C_5H_{11}-$ | $n-C_5H_{11}-$ | 23(C→S) 135(S⇌N) 136(N⇌I) |

In Table 1, C represents a crystalline phase; S, a smectic phase; N, a nematic phase; I, an isotropic liquid phase; and the arrow, phase transition.

The compounds of formula (I) in accordance with this invention are nematic liquid crystalline compounds having weakly negative dielectric anisotropy. Hence, a mixture of the compound of formula (I) with another nematic liquid crystalline compound having negative or weakly positive dielectric anisotropy can be used as a material for a dynamic scattering mode display cell, and a mixture of the compound of formula (I) with another nematic liquid crystalline compound having strongly positive dielectric anisotropy can be used as a material for a field effect mode display cell.

Typical examples of preferred compounds which can be used in admixture with the compounds of formula (I) include phenyl 4,4'-substituted benzoates, phenyl 4,4'-substituted cyclohexanecarboxylates, diphenyl 4,4'-substituted cyclohexanecarboxylates, 4'-substituted phenyl 4-(4-substituted cyclohexanecarbonyloxy)benzoates, 4'-substituted phenyl 4-(4-substituted cyclohexyl)benzoates, 4'-substituted cyclohexyl 4-(4-substituted cyclohexyl) benzoates, 4,4'-biphenyl, 4,4'-phenylcyclohexane, 4,4'-substituted terphenyls, 4,4'-biphenylcyclohexane, and 2-(4'-substituted phenyl)-5-substituted pyrimidines.

Table 2 below shows the N-I points and viscosities of mixed crystals composed of 80% by weight of matrix liquid crystals (A) now in widespread use as nematic liquid crystalline materials having excellent multiplex driving characteristics and 20% by weight of compound Nos. 2, 3, 4, 5, 6 and 7 respectively of formula (I), and the matrix liquid crystals (A) themselves for comparison. The matrix liquid crystals (A) consist of 40% by weight of n-C₃H₇—⟨H⟩—⟨O⟩—CN, 30% by weight of n-C₅H₁₁—⟨O⟩—⟨O⟩—CN, 15% by weight of n-C₃H₇—⟨H⟩—COO—⟨O⟩—OC₂H₅, and 15% by weight of n-C₄H₉—⟨H⟩—COO—⟨O⟩—OC₂H₅.

TABLE 2

|  | N-I point (°C.) | Viscosity (centipoises at 20° C.) |
| --- | --- | --- |
| (A) | 42.4 | 21.2 |
| (A) + (No. 1) | 54.4 | 19.8 |
| (A) + (No. 2) | 54.8 | 19.8 |
| (A) + (No. 3) | 61.0 | 19.9 |
| (A) + (No. 4) | 59.1 | 20.1 |
| (A) + (No. 5) | 61.0 | 20.3 |
| (A) + (No. 6) | 59.2 | 20.2 |
| (A) + (No. 7) | 61.1 | 20.6 |

Table 3 shows the N-I points and viscosities of mixed crystals composed of 80% by weight of matrix liquid crystals (B) which are in widespread use as are the matrix liquid crystals (A) and 20% by weight of compounds Nos. 1, 2, 3, 4, 5, 6 and 7 respectively of formula (I), and the matrix liquid crystals (B) themselves for comparison. The matrix liquid crystals (B) consist of 20% by weight of n-C₃H₇—⟨H⟩—⟨O⟩—CN, 16% by weight of n-C₅H₁₁—⟨H⟩—⟨O⟩—CN, 16% by weight of n-C₇H₁₅—⟨H⟩—⟨O⟩—CN, 8% by weight of n-C₃H₇—⟨H⟩—COO—⟨O⟩—OC₂H₅, 8% by weight of n-C₃H₇—⟨H⟩—COO—⟨O⟩—O—n-C₄H₉, 8% by weight of n-C₄H₉—⟨H⟩—COO—⟨O⟩—OCH₃, 8% by weight of n-C₄H₉—⟨H⟩—COO—⟨O⟩—OC₂H₅, 8% by weight of n-C₅H₁₁—⟨H⟩—COO—⟨O⟩—OCH₃, and 8% by weight of n-C₅H₁₁—⟨H⟩—COO—⟨O⟩—OC₂H₅.

TABLE 3

|  | N-I point (°C.) | Viscosity (centipoises at 20° C.) |
| --- | --- | --- |
| (B) | 54.0 | 21.0 |
| (B) + (No. 1) | 63.7 | 19.7 |
| (B) + (No. 2) | 64.1 | 19.7 |
| (B) + (No. 3) | 69.5 | 19.7 |
| (B) + (No. 4) | 68.3 | 20.0 |
| (B) + (No. 5) | 69.9 | 20.1 |
| (B) + (No. 6) | 68.7 | 20.0 |
| (B) + (No. 7) | 70.1 | 20.4 |

It will be seen from the data given in Tables 2 and 3 that the compounds of formula (I) decrease the viscosities of the mixed liquid crystals and increase their N-I points. The viscosity values of about 20 centipoises (20° C.) given in Tables 2 and 3 are much lower than the viscosities of various mixed crystals having an N-I point of at least 65° C. which are now on an average practical level. The compounds of formula (I) have a high utilitarian value in that they give mixed liquid crystals having such a low viscosity.

A comparative experiment described below demonstrates the advantages of the present invention.

A known compound of the following formula

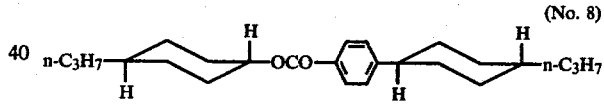

which is similar in chemical structure to the compound (I) of this invention and is used widely to increase the N-I points of mixed liquid crystals was mixed in various proportions with the matrix liquid crystals (B). Likewise, one compound of the invention having the following formula

Figure 2:
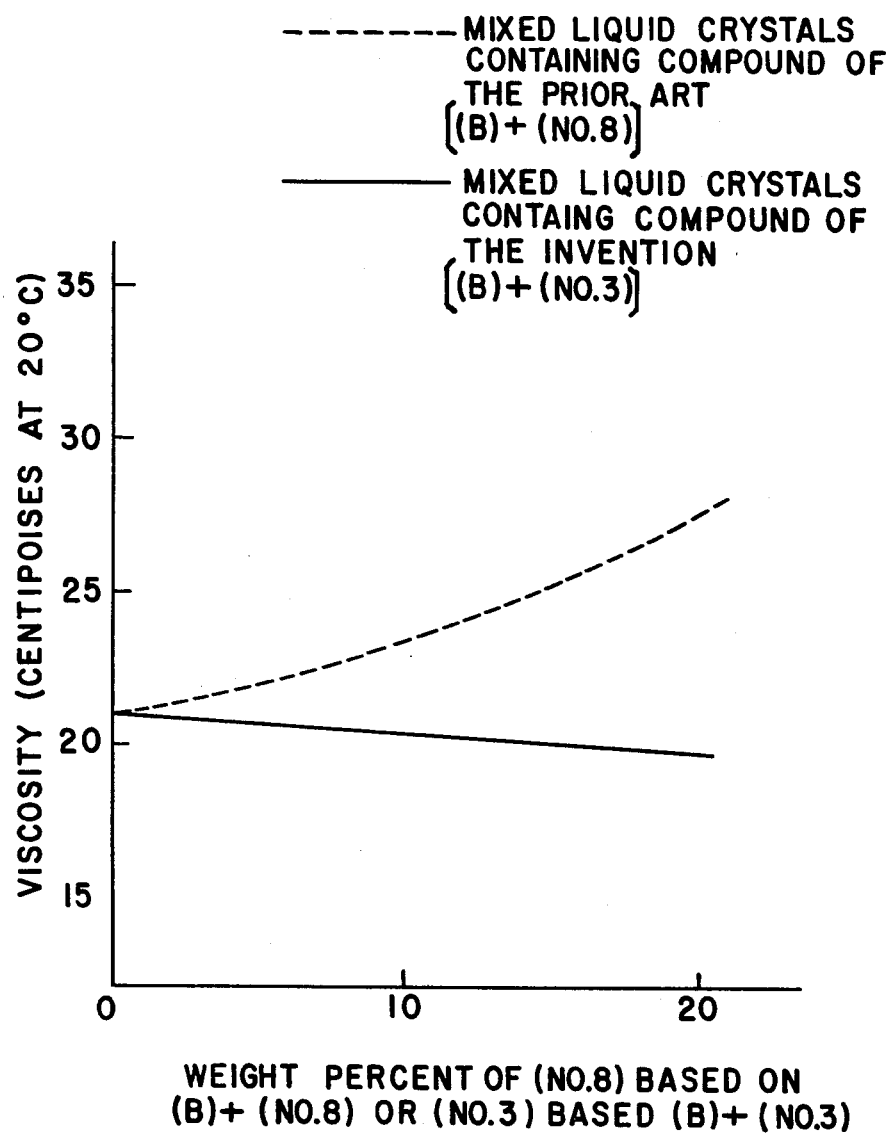
Figure 3:
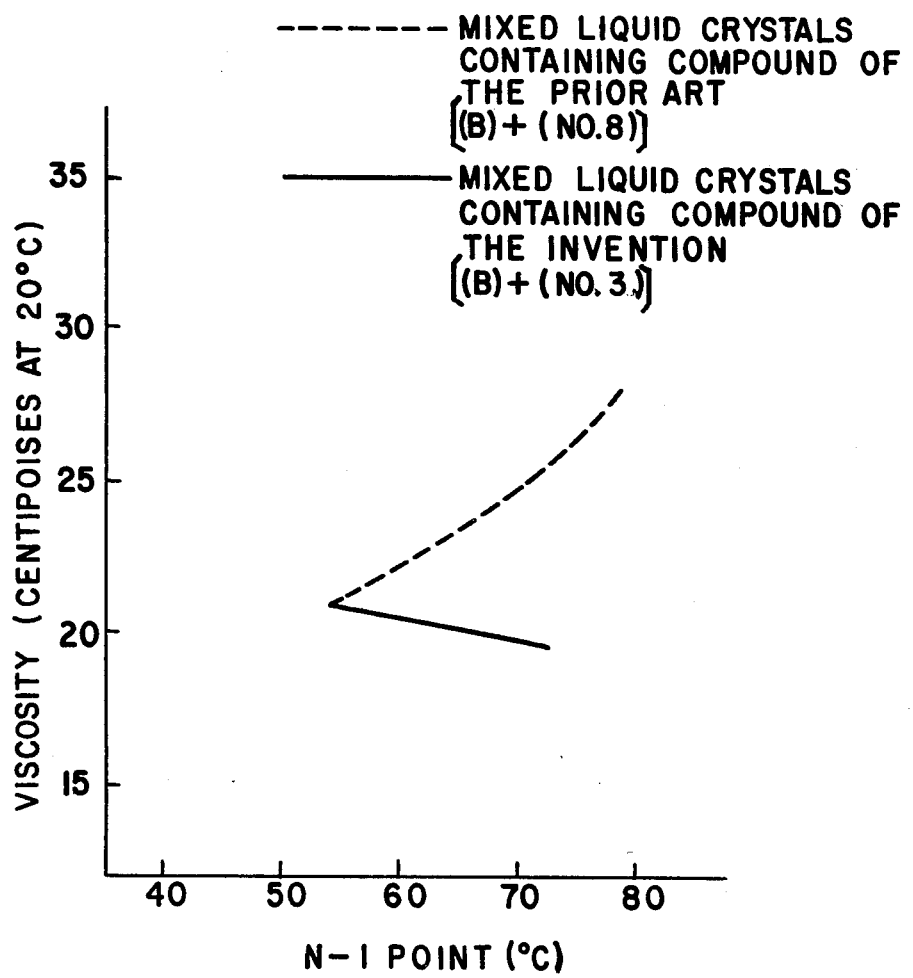

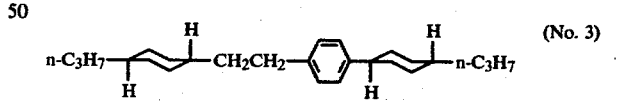

was mixed in various proportions with the matrix liquid crystals (B). The N-I points and viscosities of the resulting two types of mixed liquid crystals were measured. On the bases of the results of measurement, the relation between the N-I point of the mixed liquid crystals and the proportion of compound No. 8 or 3 is shown in FIG. 1; the relation between the viscosity of the mixed liquid crystals and the proportion of compound No. 8 or 3, in FIG. 2; and the relation between the N-I point and viscosity of the mixed liquid crystals, in FIG. 3. It will be seen from the results, especially those in FIG. 3, that the mixed liquid crystals obtained by adding the typical analogous compound of the prior art to the matrix liquid crystals increase greatly in viscosity with an increase in N-I point, whereas the mixed liquid crystals obtained by adding the compound (I) of this invention to the matrix liquid crystals decrease in viscosity with increasing N-I point.

The following non-limitative Examples illustrate the present invention more specifically.

EXAMPLE 1

Anhydrous aluminum chloride (16.0 g; 0.120 mole) was added in 100 ml of carbon disulfide, and with stirring at room temperature, 20.3 g (0.1000 mole) of trans-4-n-propylcyclohexylacetyl chloride was added dropwise. The reaction mixture was cooled to −5° C., and with stirring, 20.2 g (0.100 mole) of trans-4-n-propyl-1-phenylcyclohexane was added dropwise and reacted at −5° C. for 5 hours. The temperature was raised to room temperature, and the reaction was further carried out for 2 hours. After distilling off carbon disulfide, the reaction mixture was added to ice water. The mixture was then heated, and stirred at 60° C. for 1 hour. After cooling, the reaction mixture was extracted with ether. The extract was washed with water and dried. Ether was distilled off, and the residue was recrystallized from a mixture of n-hexane and ethanol to give 28.6 g (0.0777 mole) of the following compound.

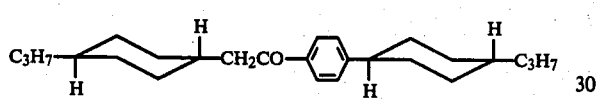

To the resulting compund were added 80 ml of triethylene glycol, 6.22 g (0.124 mole) of hydrazine hydrate and 12.9 g (0.230 mole) of potassium hydroxide. With stirring, the temperature of the mixture was gradually raised, and it was reacted at 180° C. for 3 hours. After cooling, 200 ml of water was added, and the mixture was extracted with ether. The extract was washed with water and dried over anhydrous sodium sulfate. Ether was distilled off, and the residue was recrystallized from a mixture of n-hexane and ethanol to give 23.8 g (0.0672 mole) of the following compound.

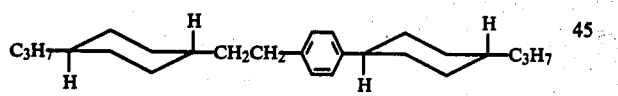

Yield: 67.2%
Transition temperatures:
  46° C. (C→S)
  106° C. (S⇌N)
  131° C. (N⇌I)

EXAMPLE 2

In a manner similar to Example 1, the following compound was obtained.

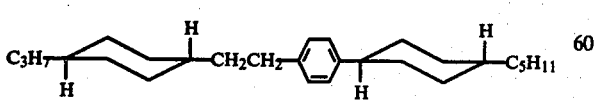

Yield: 65.0%
Transition temperatures:
  126° C. (C→S)
  131° C. (S⇌N)
  134° C. (N⇌I)

EXAMPLE 3

In a manner similar to Example 1, the following compound was obtained.

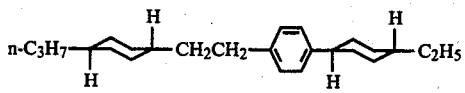

Yield: 59.8%
Transition temperatures:
  58° C. (C→S)
  78° C. (S⇌N)
  105° C. (N⇌I)

EXAMPLE 4

In a manner similar to Example 1, the following compound was obtained.

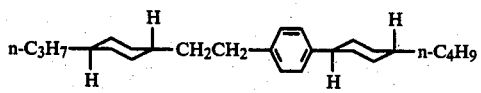

Yield: 64.2%
Transition temperatures:
  35° C. (C→S)
  117° C. (S⇌N)
  126° C. (N⇌I)

EXAMPLE 5

In a manner similar to Example 1, the following compound was obtained.

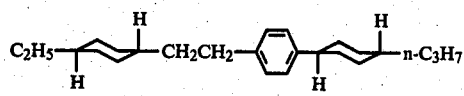

Yield: 60.8%
Transition temperatures:
  71° C. (C→S)
  81° C. (S⇌N)
  103° C. (N⇌I)

EXAMPLE 6

In a manner similar to Example 1, the following compound was obtained.

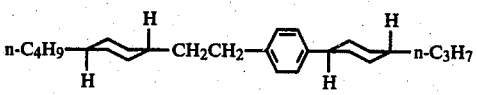

Yield: 61.8%
Transition temperatures:
  24° C. (C→S)
  114° C. (S⇌N)
  128° C. (N⇌I)

EXAMPLE 7

In a manner similar to Example 1, the following compound was obtained.

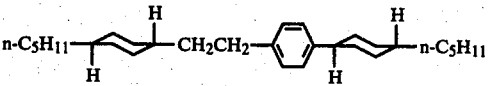

Yield: 62.9%

Transition temperatures:

23° C. (C→S)

135° C. (S⇌N)

136° C. (N⇌I)

What we claim is:

1. A 1-cyclohexyl-2-cyclohexylphenylethane derivative of the following general formula

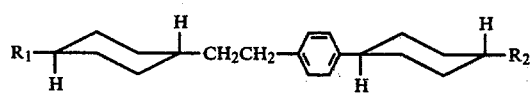

wherein $R_1$ and $R_2$, independently from each other, represent a linear alkyl group having 1 to 7 carbon atoms.

2. The derivative of claim 1 wherein $R_1$ is an ethyl group and $R_2$ is a n-propyl group.

3. The derivative of claim 1 wherein $R_1$ is a n-propyl group and $R_2$ is an ethyl group.

4. The derivative of claim 1 wherein both $R_1$ and $R_2$ are n-propyl groups.

5. The derivative of claim 1 wherein $R_1$ is a n-propyl group and $R_2$ is a n-butyl group.

6. The derivative of claim 1 wherein $R_1$ is a n-propyl group and $R_2$ is a n-pentyl group.

7. The derivative of claim 1 wherein $R_1$ is a n-butyl group and $R_2$ is a n-propyl group.

8. The derivative of claim 1 wherein both $R_1$ and $R_2$ are n-pentyl groups.

* * * * *

UNITED STATES PATENT AND TRADEMARK OFFICE
CERTIFICATE OF CORRECTION

PATENT NO. : 4,393,258
DATED : July 12, 1983
INVENTOR(S) : Hisato Sato, et al.

It is certified that error appears in the above—identified patent and that said Letters Patent is hereby corrected as shown below:

Please amend as follows:

Title page, [73], Assignee: delete "Dainippon Mk & Chemicals Inc.," and insert

-- Dainippon Ink & Chemicals, Inc., --

Signed and Sealed this

Eighteenth Day of October 1983

[SEAL]

Attest:

GERALD J. MOSSINGHOFF

Attesting Officer    Commissioner of Patents and Trademarks

Notice of Adverse Decision in Interference

In Interference No. 101,265, involving Patent No. 4,393,258, H. Sato, H. Takatsu, Y. Fujita, M. Tazume, K. Takeuchi and H. Ohnishi, 1-CYCLOHEXYL-2-CYCLOHEXYLPHENYLETHANE DERIVATIVES, final judgment adverse to the patentees was rendered Sept. 24, 1985, as to claims 1–8.
*[Official Gazette November 26, 1985.]*